(12) United States Patent  (10) Patent No.:　US 7,101,341 B2
Tsukashima et al.  (45) Date of Patent:　*Sep. 5, 2006

(54) RESPIRATORY MONITORING, DIAGNOSTIC AND THERAPEUTIC SYSTEM

(76) Inventors: Ross Tsukashima, 13670 Danielson St., Suite F, Poway, CA (US) 92064; Jeffery D. Schipper, 13670 Danielson St., Suite F, Poway, CA (US) 92064; Leo R. Roucher, Jr., 13670 Danielson St. Suite F, Poway, CA (US) 92064; Erich H. Wolf, 13670 Danielson St. Suite F, Poway, CA (US) 92064

( * ) Notice: Subject to any disclaimer, the term of this patent is extended or adjusted under 35 U.S.C. 154(b) by 204 days.

This patent is subject to a terminal disclaimer.

(21) Appl. No.: 10/413,701

(22) Filed: Apr. 15, 2003

(65) Prior Publication Data

US 2004/0210151 A1　Oct. 21, 2004

(51) Int. Cl.
　　*A61B 5/00*　(2006.01)
(52) U.S. Cl. .......................... 600/532; 73/23.3; 422/84
(58) Field of Classification Search ................ 600/532; 73/23.3; 422/84
See application file for complete search history.

(56) References Cited

U.S. PATENT DOCUMENTS

| | | |
|---|---|---|
| 3,946,726 A | 3/1976 | Pikui |
| 3,991,304 A | 11/1976 | Hillsman |
| 4,098,650 A * | 7/1978 | Sayles ........................ 205/788 |
| 4,366,821 A | 1/1983 | Wittmaier et al. |
| 5,042,501 A | 8/1991 | Kenny et al. |
| 5,069,220 A | 12/1991 | Casparie et al. |
| 5,081,871 A | 1/1992 | Glaser |
| 5,140,993 A | 8/1992 | Opekun, Jr. et al. |
| 5,174,959 A | 12/1992 | Kundu et al. |
| 5,213,109 A | 5/1993 | Susi |
| 5,265,595 A | 11/1993 | Rudolph |
| 5,327,901 A | 7/1994 | Delente |
| 5,361,772 A | 11/1994 | Murnick et al. |
| 5,388,571 A * | 2/1995 | Roberts et al. ........ 128/203.12 |
| 5,432,094 A | 7/1995 | Delente |
| 5,447,165 A * | 9/1995 | Gustafsson .................. 600/532 |
| 5,465,728 A | 11/1995 | Philips |
| 5,645,049 A | 7/1997 | Foley et al. |
| 5,676,154 A | 10/1997 | Pettersson |
| 5,795,787 A | 8/1998 | Silkoff et al. |
| 5,826,577 A | 10/1998 | Perroz, Jr. et al. |
| 5,857,460 A | 1/1999 | Popitz |
| 5,922,610 A | 7/1999 | Alving et al. |
| 5,962,335 A | 10/1999 | Katzman |
| 6,010,459 A | 1/2000 | Silkoff et al. |
| 6,033,368 A | 3/2000 | Gaston, IV et al. |
| 6,053,874 A | 4/2000 | Kharitonov et al. |
| 6,067,983 A | 5/2000 | Stenzler |
| 6,180,414 B1 | 1/2001 | Katzman |
| 6,186,958 B1 | 2/2001 | Katzman et al. |

(Continued)

*Primary Examiner*—Robert L. Nasser
(74) *Attorney, Agent, or Firm*—Michael Klicpera

(57) ABSTRACT

Disclosed is a system and method for monitoring, diagnosing, and treating certain respiratory conditions, such as asthma. The system includes a mask apparatus fitted with a pH sensor and thermocouple, a continuous positive airway pressure (CPAP) device, a processing receiver, and a therapeutic nebulizer/atomizer/humidifier device. The mask apparatus, CPAP device and therapeutic nebulizer/atomizer/humidifier device are connected by a pneumatic means. The pH sensor and the thermocouple are in electrical communication with the processing receiver that controls, through an electronic means, the CPAP device and therapeutic nebulizer/atomizer/humidifier device. The electrical communications can be in the form of a plurality of wires or employ wireless means.

38 Claims, 6 Drawing Sheets

U.S. PATENT DOCUMENTS

| | | |
|---|---|---|
| 6,213,955 B1 | 4/2001 | Karakasoglu et al. |
| 6,221,026 B1 | 4/2001 | Philips |
| 6,312,390 B1 | 11/2001 | Philips |
| 6,398,739 B1 | 6/2002 | Sullivan et al. |
| 6,419,634 B1 | 7/2002 | Gaston, IV et al. |
| 6,479,019 B1 | 11/2002 | Goldstein et al. |
| 6,491,643 B1 | 12/2002 | Katzman et al. |
| 6,540,691 B1 | 4/2003 | Philips |
| 6,582,376 B1 | 6/2003 | Baghdassarian |
| 6,585,661 B1 | 7/2003 | Hunt et al. |
| 6,599,253 B1 | 7/2003 | Baum et al. |
| 6,612,306 B1 | 9/2003 | Mault |
| 6,620,107 B1 * | 9/2003 | Payne et al. ................ 600/532 |
| 6,648,833 B1 * | 11/2003 | Hampton et al. ........... 600/532 |
| 2003/0013695 A1 | 1/2003 | Hunt et al. |
| 2003/0023389 A1 | 1/2003 | Rothe et al. |
| 2003/0134427 A1 | 7/2003 | Roller et al. |
| 2003/0208133 A1 * | 11/2003 | Mault ......................... 600/532 |
| 2004/0077965 A1 * | 4/2004 | Hubbard et al. ............ 600/532 |
| 2004/0162500 A1 * | 8/2004 | Kline ......................... 600/532 |

\* cited by examiner

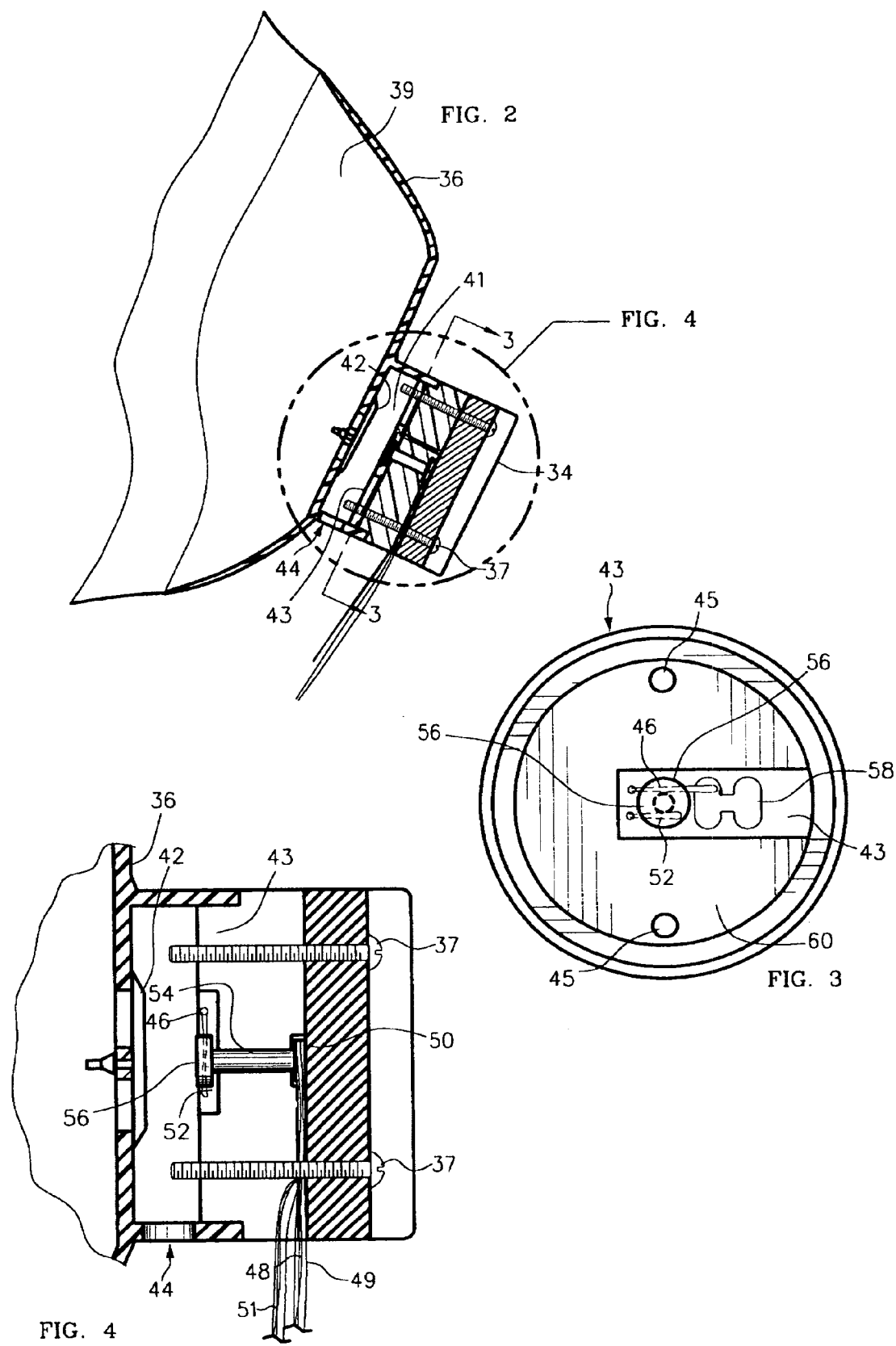

RESPIRATORY MONITORING, DIAGNOSTIC AND THERAPEUTIC SYSTEM

FIELD OF THE INVENTION

The field of art to which this invention relates is in the monitoring of certain parameters and transfer of such information to facilitate the diagnosis or therapeutic treatment for patients suffering from respiratory diseases, such as asthma Laryngopharyngeal reflux (LPR). More specifically, the present invention monitors the pH level of a patient's breath and provides data for determining the frequency and volume of a therapeutic dose to be administered to the patient's airways.

BACKGROUND OF THE INVENTION

Recently, it has been reported that the monitoring of acidity or pH of a patient's breath could help physicians in estimating the degree of air passage inflammation now considered a key contributor to asthma and other respiratory conditions. Asthma is characterized by symptoms of wheezing, coughing, chest tightness, and shortness of breath. Manifestations include constriction (the tightening of the muscles around the airways) and inflammation (the swelling and irritation of the airways) that can be triggered through exposure to smoking, dust mites, pets, activity, cold, infection, weather, pollen, etc.

A clinical study of people with chronic obstructive pulmonary disease (COPD), bronchiectasis and asthma demonstrated more acidic levels in COPD and bronchiectasis patients, which is indicative of the chronic inflammation that these patients experience. This study also observed an increased acidic level measured from the breath of patients suffering from moderate asthma when compared to mild forms of the disease. It was also found that the asthmatic's breath was much more acidic during asthma attacks, but normalized after anti-inflammatory medication was administered.

This data suggests that the monitoring of an asthmatics' breath for pH might be an effective way to measure the degree of inflammation in the air passages. Furthermore, this data suggests that close monitoring of an asthmatic's breath pH could lead to prompt and effective treatment, minimizing the occurrence of asthma attacks and providing overall better asthma management.

It is estimated that 18–26 million people in the United States suffer from asthmatic conditions ranking this disease as the 8$^{th}$ worst chronic condition in the United States. It is also believed that over 5.6 million of these asthma sufferers are under the age of 18.

Studies have also shown that gastro-esophageal reflux disease (GER) affects approximately 40% of the US Adult Population and that 60–80 percent of all asthma patients have (GER). Gastro-esophageal reflux is a condition in which gastric acid refluxes from the stomach and into the esophagus. Frequent reflux episodes may result in a potentially severe problem known as gastro-esophageal reflux disease. (GER) is the most common cause of dyspepsia or heartburn. (GER) can also manifest in the micro-aspiration of acid from the esophagus and into the airway and lungs, damaging tissue, and causing irritation of the vagus nerve. This irritation of the vagus nerve, which is common to both the esophagus and the bronchial tree, can cause constriction of the airway. Acid reflux above the lower esophageal sphincter and can cause anatomical damage, and is linked to sleep disordered breathing. It has also been found that bronchial dilator drugs can relax the lower esophageal sphincter and trigger GERD induced asthmatic conditions. Sleep apnea has also been found to trigger reflux events. Testing for GER and the diagnosis of GERD are typically accomplished by measuring pH with catheter based devices.

These current pH monitoring methods suffer from the following drawbacks: 1) the current method requires an invasive procedure to place a pH measurement catheter or implanted pH measurement capsule in the patient's esophagus, 2) the procedure is not well tolerated by some patients, 3) the catheter or capsule placement must be performed by a physician, 4) the capsule cannot be placed above the Upper Esophageal Sphincter (UES) to measure airway pH, and 5) there are no defined standards for evaluation of pH above the UES.

Accordingly, there is a need in this art for a novel, pH diagnostic and monitoring system with electronic or wireless communication linked to a processing receiver that can also be used to activate a therapeutic nebulizer/atomizer/humidifier for treating asthmatic or other respiratory conditions.

SUMMARY OF THE INVENTION

The present invention pertains to an invention for monitoring the pH level of a patient's breath in a typical mask that provides a means for transferring this data to a processing receiver for diagnosing disease abnormalities and determining the frequency and volume of a therapeutic dose to be administered to a patient, typically with a respiratory condition such as asthma. Monitoring of a patients' breath chemistry is provided by a system that includes a miniaturized pH sensor, provides for real-time monitoring of patient airway pH values, and utilizes solid state cooling to precipitate moisture from a patient's breath.

A general respiratory mask is mounted with a miniaturized pH sensor and data transfer means e.g. direct wiring or by providing a transmitter with an antenna for wireless transferring of the pH data to a processing receiver. The temperature of the pH sensor is lowered below the dew point of the exhaled patient breath by a solid-state Peltier junction engaged on one side to a heat sink. A thermocouple is provided to monitor the temperature of the sensor for more accurate pH calculations. Keeping the sensor temperature below the dew point will cause the patient's exhaled breath to condense as a liquid in close proximity to the surface of the sensor. It is commonly known that monitoring of pH is significantly more accurate if measuring a condensed liquid. A transmitter with an antenna transfers the observed pH data by employing one of many wireless methods, such as radio-frequency (RF) energy. Alternately, the transfer of observed pH data is accomplished by direct wire methods.

The pH data is transferred or updated at specific intervals, which can be varied according to the patient's needs, to the processing receiver that is engaged to the treatment and humidifier apparatuses. The processing receiver computes and diagnoses the chemistry data and determines what apparatus and at what frequency it should be activated.

The present invention mask is also fitted with a means to remove the condensed liquid through an exhaust port or the connected pneumatic hose to remove unnecessary and accumulated breath condensate.

These and other features, aspects and advantages of the present invention will become better understood with reference to the following descriptions and claims.

BRIEF DESCRIPTION OF THE DRAWINGS

FIG. 2 is a sectional side view of the general mask apparatus demonstrating in more detail of the orientation and components of the mask, and pH sensing means.

FIG. 3 is a sectional view taken from FIG. 1 demonstrating the general location of the pH sensor, cooling shank, thermocouple and fluid pool on the sampling plate for condensing and containing a patient's breath.

FIG. 4 is a sectional side view taken from FIG. 2 demonstrating in more detail the relative locations of the heat sink, Peltier junction, body and head of cooling transfer shank, thermocouple, and pH sensor.

FIG. 6 is an electrical schematic of the general components in the processing receiver.

FIGS. 7 and 8 are flowcharts showing the sequential computational steps employed by the processing receiver.

DESCRIPTION OF THE PREFERRED EMBODIMENTS

The present invention provides a system and method for monitoring physiological parameters from a patient's exhaled breath and communicates this information to a processing computer/receiver that diagnoses the information. The system can use computational instructions to activate and de-activate an electrically connected treatment nebulizer/atomizer/humidifier device, and can be integrated with a continuous positive airway pressure (CPAP) device.

FIG. 1 illustrates that the present invention is a system 10 comprised of several components. As shown in the Figure, a typical mask apparatus 36 is fitted with a securing strap or typical headgear apparatus 38. The typical mask apparatus 36 is generally fabricated from a polymeric and/or silicone material and configured to fit over a patient's nose, or nose and mouth, to assist in breathing conditions. The securing strap 38 is made from a flexible material and is positioned around the patient's head such that the mask substantially engages the patient's face and mouth area, minimizing ambient air from entering the boundaries of the mask. It is contemplated by the Applicants that other mask configurations and types can be employed with the present invention to achieve the goal of monitoring, diagnosing and treating respiratory conditions in patients.

Shown attached to the front of the typical mask apparatus 36 is a heat sink 34 with made generally from a material that has good heat conduction properties, such as certain metallic elements and alloys. Some candidates for the heat sink 34 and fins 35 are aluminum, copper, silver and gold. The heat sink 34 is fitted with fins 35 to increase the surface area of the heat sink 34 to dispense heat generated by the system. The heat sink 34 is shown secured to the mask by screws 37 but can also be attached with other commonly known methods, such as adhesives.

The typical mask apparatus 36 is connected to the exit port 22 of a CPAP device 16 by means of a pneumatic hose 18. The hose can be manufactured from a variety of materials, including polymers such as polyethylene, polypropylene, polyvinyl chloride or silicone. The material used for the hose should be resistant to water and acidic environments, and should not interfere or interact with any medicaments employed in the present invention. CPAP air exits port 22 and travels along the length of the pneumatic host 18 to the internal sampling cavity created by the general mask apparatus covering the patient's face. The CPAP device has a control means 20 for increasing and decreasing the volume of air generated by the apparatus and the output an optional humidification device. The CPAP device and humidifier are powered by an electrical source such as a standard plug 12 and cable 14.

Shown connected to the heat sink 34 is an electrical wire 29 that communicates with a processing receiver 26.

Electrical wire 29 is typical in that the internal core comprises an electrical conductive metallic material and is encased by a nonconductive jacket. Processing receiver 26 is connected to the CPAP device 16 by an electrical wire 24 for controlling the activation of air generated by the CPAP device 16 and transferred to the typical mask apparatus 36. Also, an electrical connection by means of a wire 31 to the processing receiver 26 is a treatment nebulizer/atomizer/humidifier device 32. As an alternate method, a wireless means 40 can be utilized instead to communicate between the processing receiver 26 with an antenna 28 to the treatment nebulizer/atomizer/humidifier device 32. Although not shown in detail in FIG. 1, a wireless means also can be employed to communicate between the typical mask apparatus 36 and the processing receiver 26. In addition, a wireless means also can be employed to communicate between the processing receiver 26 and the CPAP device 16. As appreciated by those skilled in the art, wireless means for communicating between various components can be accomplished using radio frequency waves, microwaves, ultrasonic waves, or light optics.

The treatment nebulizer/atomizer/humidifier device 32 is pneumatically connected to hose 18 at some point along its length between the CPAP device 16 and the typical mask apparatus 36. The treatment nebulizer/atomizer/humidifier device 32 has a medicament storage chamber 33 where various types of therapeutic medicaments can be delivered to the pneumatic system and to the patient at intervals commanded by the processing receiver 26.

FIG. 2 illustrates a sectional side view of the general mask apparatus demonstrating in more detail the orientation and components of the mask 36, the heat sink 34 and the pH sensing means 46. When deployed, the mask forms a sampling chamber 39 between the mask 36 and the patient's facial area that is in pneumatic connection with the patient's respiratory system. This sampling chamber 39 contains a current sample of the patient's breath that enters, through a one-way valve 42, and into the condensing chamber 41 formed between the exterior mask surface and the back surface of the heat sink apparatus. The heat sink is mounted to the mask apparatus 36 by screws 37 or alternatively using adhesive or other mounting technology.

FIG. 3 is a sectional view taken from FIG. 1 demonstrating the general location of the pH sensor, cooling shank, thermocouple and fluid pool on the sampling plate for condensing and containing a patient's breath. The sampling plate 43 functions to condense the patient's breath and form a pool of liquefied breath such that the sensor is immersed in liquid and monitors the pH level. The sampling plate 43 is generally manufactured from a material that has good heat conduction properties, such as certain metallic elements and alloys. Some candidates are aluminum, copper, silver and gold. FIG. 3 shows the general location of the pH sensor 46, cooling shank head 56, thermocouple 52 and fluid pool area 58 for containing condensed breath. The pH sensor 46 is comprised from a metallic antimony or similar alloy that is fitted with a plurality of wires or wireless means to communicate the analog pH information monitored by the sensor to a processing receiver 26. Similarly, the thermocouple is fabricated from standard metallic components and is fitted with a plurality of wires or wireless means to communicate the analog temperature information monitored by the thermocouple to the processing receiver 26. The cooling shank head 56 is part of a cooling shank that penetrates the sampling plate 43 and ultimately engages the Peltier junction 50 (see FIG. 4). The cooling head 56 and body shank 54 (see FIG. 4) is fabricated generally from a material that has good heat conduction properties, such as certain metallic elements and alloys. Some candidates are aluminum, copper, silver and gold. The cooling head 56 is engaged to and reduces the temperature of the sampling plate 43 and pooling area 58 to facilitate the condensation of breath into a liquid that pools in the pooling area 58 that covers and becomes exposed to the pH sensor 46. Shown here, both the thermocouple 52 and the pH sensor 46 are mounted within a lumen formed within the cooling shank head 56. The thermocouple 52 is shown residing within the cooling shank head 56. The pH sensor extends beyond the cooling head 56 and into the pooling area 58. The Applicant contemplates that other mounting positions for the thermocouple 52 and pH sensor 46 can be employed without sacrificing any performance. For example, the sensor 46 can be mounted such that the head of the sensor enters the pooling area from the bottom and extends back through the back side of the sampling plate 43, as shown in FIG. 4. If appropriate, holes 45 in sampling plate 43 can be threaded to receive screws 37.

Within the collection region 47, the pooling area 58 shown in FIG. 3 portrays a dumbbell shape. It is contemplated by the Applicant that various other shapes, side curvatures and dimensions may be employed to facilitate capturing the condensed breath and forming a pool of liquid that immerses the head of the pH sensor 46.

Figure 1:
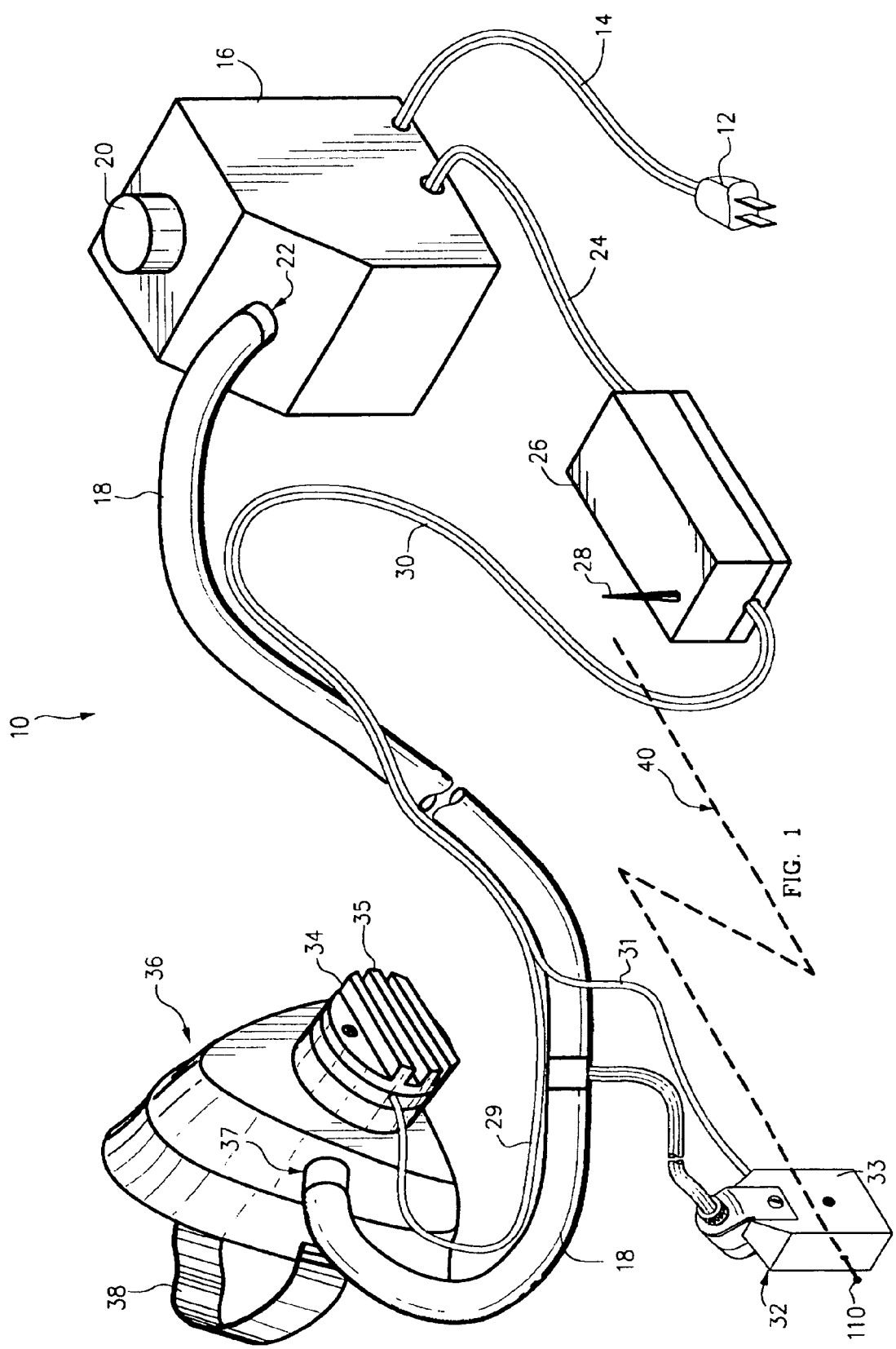
FIG. 1 is a perspective representation of the present invention systems, showing the various components of the system, including a mask apparatus fitted with a heat sink and pH sensing means, a continuous positive airway pressure (CPAP) device connected to the mask apparatus, a processing receiver electrically connected to the mask apparatus, and a nebulizer/atomizer/humidifier device electrically connected to the processing receiver.

FIG. 4 illustrates a sectional side view taken from FIG. 1 demonstrating in more detail the relative locations of the heat sink 34, the solid-state Peltier junction 50, body 54 and head 56 of cooling transfer shank, thermocouple 52, and pH sensor 46. As shown in this figure, the Peltier junction 50 engages the backside of heat sink 34. The Peltier junction 50 is connected by wires 51 to a DC power source, such as a battery (not shown) that generally is in the range of 0.5 to 12 volts. The Peltier junction functions as a heat pump, removing heat from the cooling body shank 54 and head 56, thereby reducing its relative temperature, and transferring the heat to the heat sink 34 and fins 35 that dissipates it into the environment. As the Peltier junction reduces the temperature of the cooling head and associated components, the adjoining pooling area 58 and sampling plate 43 temperatures are also reduced. The net effect of this operation is that the these metallic surfaces have a temperature lower than the dew point, which causes the sampled breath to condense and form a pool of liquefied breath in the pooling area 58.

Electronic communication from the pH sensor wires 48 and the thermocouple wires 49 that are further connected to a wire or wireless means for communication to the processing receiver 26. In the case of a wireless means, wires 48 and 49 would terminate in an antenna (not shown) and communicate with an antenna associated with the processing receiver 26.

Alternatively, a non-liquid pH sensing means, by which a direct pH measurement of non-condensed breath may be utilized, is contemplated by the Applicants.

Figure 5:
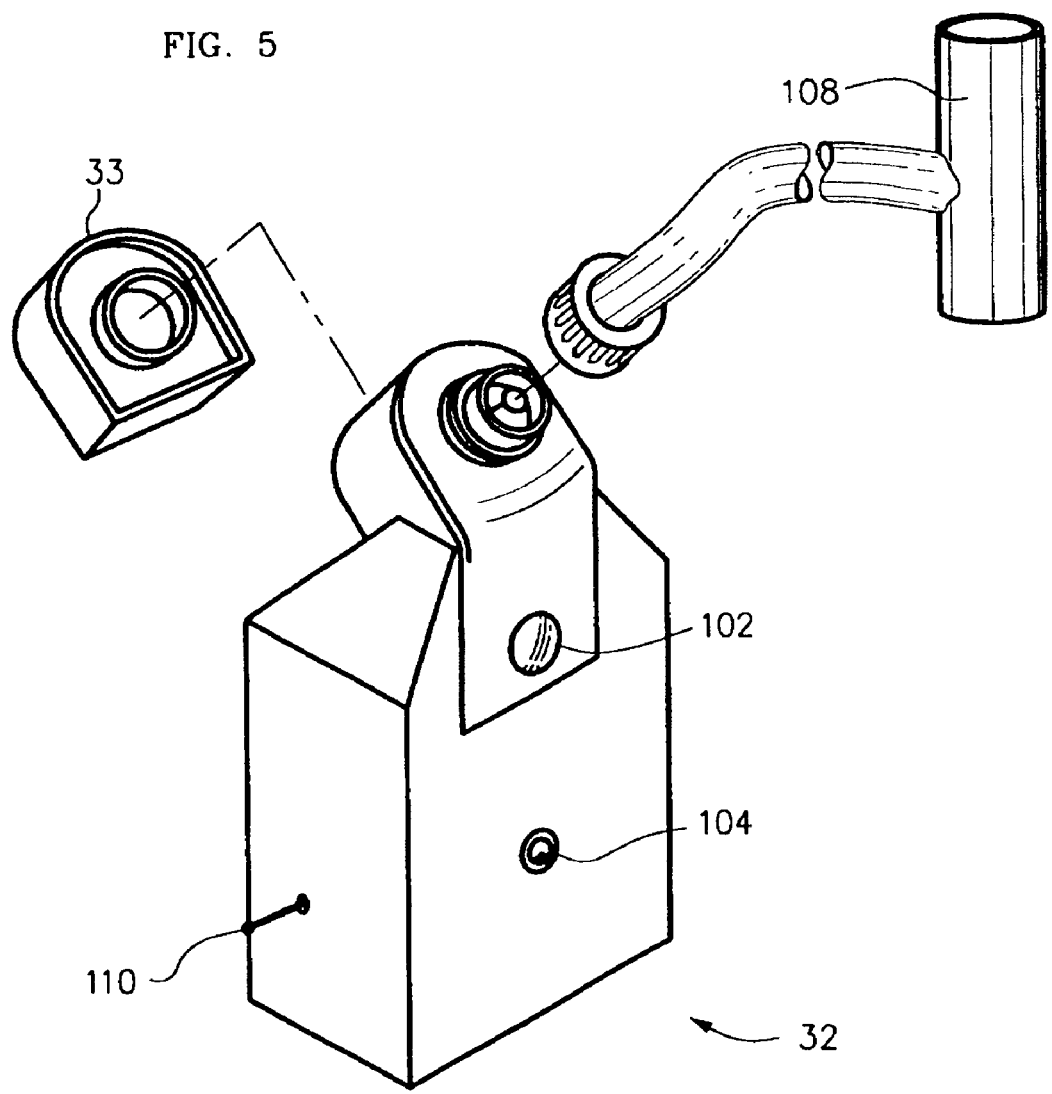
FIG. 5 is a schematic representation of the treatment nebulizer/atomizer/humidifier device, demonstrating a base unit having an on/off switch, operating lights, a medicament storage container, and interconnection for attaching the pneumatic hose.

FIG. 5 is a schematic representation of the treatment nebulizer/atomizer/humidifier device 32, demonstrating a base unit having a on/off switch 102, operating lights 104, a medicament chamber 33, and interconnection 108 for attaching to the pneumatic hose 18. The treatment nebulizer/atomizer/humidifier device 32 has an outer shell surrounding various mechanical and electrical components that function to deliver the therapeutic dose. The shell can be made of a variety of materials, including plastics such as polyethylene, polystyrene, ABS, nylon, delrin, or polyethylene terephthalate (PET). The treatment nebulizer/atomizer/humidifier device 32 communicates with the processing receiver by direct wiring (not shown) or by use of wireless means employing an antenna means 110. The base unit and various components of the treatment nebulizer/atomizer/humidifier can be fabricated from polymeric or metallic materials. Operating light 104 can consist of LED, LCD, fluorescent, or halide or other means to communicate such conditions, as on/off, medicament chamber empty, etc. Also, the Applicant contemplates a plurality of operating lights can be employed having different functions. The art associated with atomization of particles and humidification processes are known in the art. Many commercially available units can satisfy the basic requirements for the treatment nebulizer/atomizer/humidifier device 32. One such device is the MicroAir portable ultrasonic nebulizer manufactured by Omron Healthcare, Inc. of Vernon Hills, Ill. This device can be modified or fabricated so that 1) it can be remotely activated by the processing receiver 26, and 2) adapted to connect to the pneumatic tube by an appropriate connection 108 as shown in FIG. 5.

The medicament chamber 33 can contain liquid, gaseous or powdered therapeutics that the treatment nebulizer/atomizer/humidifier device 32 is designed to administer to the pneumatic system upon instructions from the processing receiver 26. One example of a medicament that can be used for treatment of an acidic condition of the patient is sodium bicarbonate. It is contemplated that the medicament chamber 33 could include a plurality of medicaments in various compartments in the medicament chamber 33. It is also contemplated that treatment nebulizer/atomizer/humidifier device 32 can select to administer one or more, or in a combination, multiple medicaments stored in the medicament chamber 33.

Figure 6:
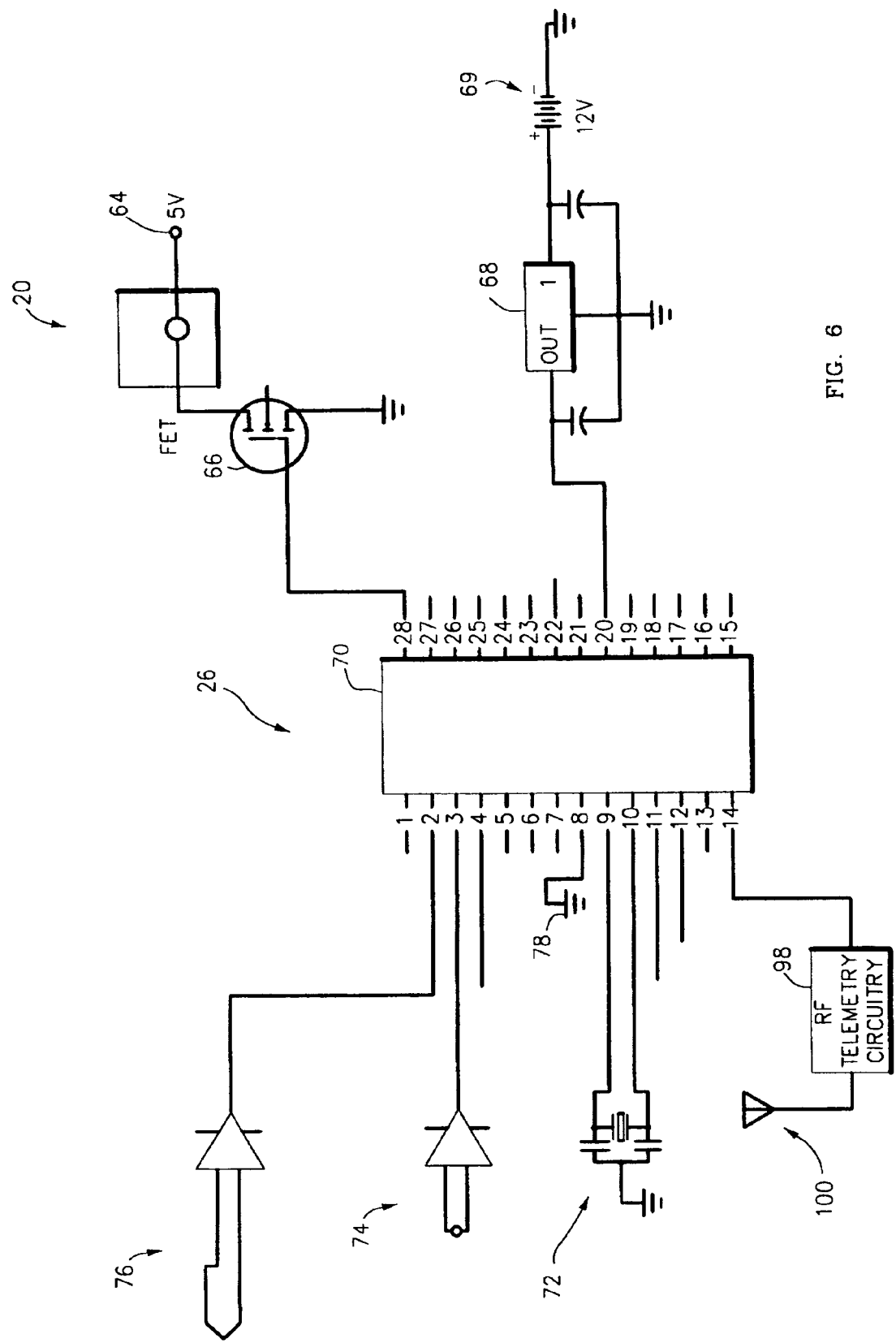

FIG. 6 is a simplified electrical schematic of the general components in the processing receiver 26. In the center is the microprocessor 70 that processes the information supplied by the thermocouple and sensor and use internal instructions to control other devices. The microprocessor 70 is instructed to communicate the chemical parameter in real-time under a sampling frequency from said sensor to the microprocessor 70 (computer) receiver. The microprocessor has an EEPROM memory section that allows for specific programming to be incorporated as processing instructions. Furthermore, the microprocessor must have the capability to convert analog signals into digital information for decoding and processing. An example of a microprocessor that could be used in the processing receiver 26 is the PIC16F876 28-pin 8-Bin CMOS FLASH microcontrollers manufactured by Microchip Technology, Inc. This particular microprocessor has a 128K EEPROM Data memory bank for flash memory of specific instructions and utilizes a 35-word instruction set. It also has five 10-bit Analog-to-Digital Inputs that are necessary for converting the information obtained from the pH sensor 46 and thermocouple 52 from its analog format into a digitized form for processing by the instruction sets of the microprocessor 70.

The microprocessor 70 includes a timing crystal 72 used for clocking operations and is connected to and energized by an approximate 12 volt power supply 69. Also included in the circuit is a power transistor 66 with an electrical connection to the 12-volt power supply, a 5-volt regulator 68, and a ground 78.

The sensor analog data that is communicated either through direct wiring or through a wireless means that is then amplified by a circuit 74 and connected to the microprocessor 70 through one of the analog-to-digital modules.

In addition, the thermocouple analog data that is communicated either through direct wiring or through a wireless means that is amplified by circuit 76 and connected to the microprocessor 70 through another one of the analog-to-digital modules.

In certain embodiments, the transmitted data can be recorded, compressed and stored as it is received using a memory chip set or memory circuit within the microprocessor (not shown). Subsequently, the data stored can be downloaded into an external data retrieval device, which can be a computer or other analysis machine.

Figure 7:
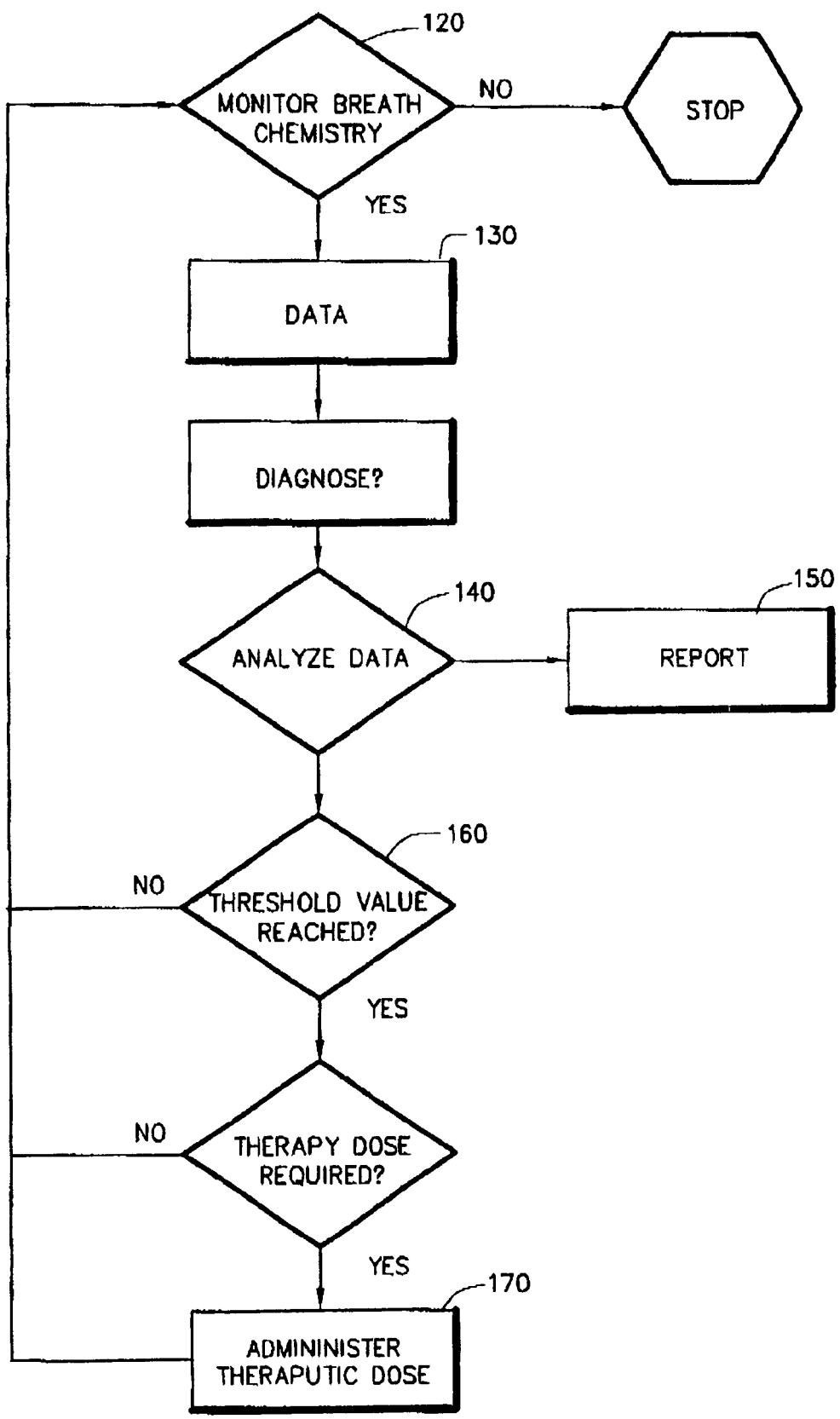
Figure 8:
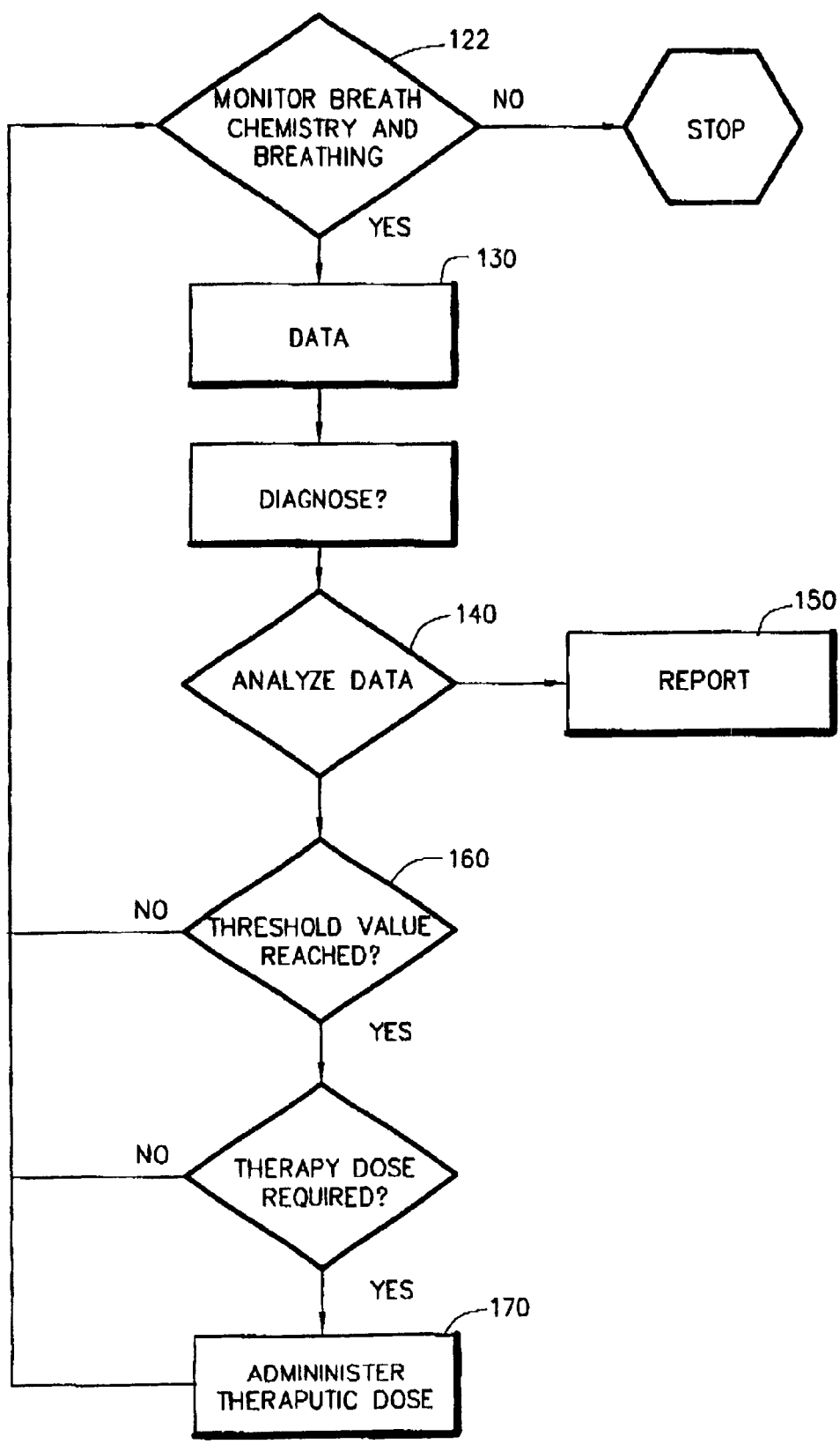

FIGS. 7 and 8 illustrate flowcharts showing the sequential computational steps employed by the processing receiver 26. As described above, the microprocessor 70 has an EEPROM memory section that allows for specific programming to be incorporated as processing instructions. The steps programmed in the microprocessor 70 are outlined in the flowcharts, starting with the 1) monitoring of breath chemistry 120 without CPAP support (FIG. 7) 2) the monitoring of breath chemistry and breathing rates (122) when CPAP supported (FIG. 8). The analog information obtained from the sensor and the thermocouple is converted to digital information and transferred to the microprocessor. The microprocessor uses the thermocouple data to calculate an accurate pH level that is stored in a registry. Optionally, this data can be diagnosed by the microprocessor 140 and stored in a memory bank whereby the microprocessor can create diagnostic reports 150.

The stored data is then compared to a threshold value or range 160 programmed in the instruction set of the microprocessor 70. For example, if the pH level does not reach the threshold value, then no actions are performed and the instruction set loops back to read breath chemistry (FIG. 7) or breath chemistry and monitor breathing rates (FIG. 8). If the pH level reaches the threshold value, then the microprocessor 70 determines the appropriate therapy 170.

These computational steps can be continued over and over again to detect, record, analyze and administer the appropriate therapeutic regime to manage patients with certain respiratory conditions.

The present invention will: 1) Monitor; 2) Diagnose; 3) Treat a respiratory disease, with and without CPAP therapy.

While the invention has been described in detail and with reference to specific embodiment thereof, it will be apparent to one skilled in the art that various changes and modifications can be made therein without departing from the spirit and scope thereof.

We claim:

1. A system for monitoring a respiratory condition:
    an apparatus for exposing a sensor to an individual's breath;
    said sensor in close proximity to an electronically activated cooling means, said cooling means functions to reduce the temperature of said sensor below the dew point of said individual's breath;
    a processing receiver; and
    said sensor providing a continuous, real-time signal indicative of breath chemistry to said receiver.

2. The system as recited in claim 1, wherein said apparatus is a general mask.

3. The system as recited in claim 1, wherein said sensor is designed to monitor pH.

4. The system as recited in claim 1, wherein said respiratory condition is asthma.

5. The system as recited in claim 1, wherein said communication is accomplished by a plurality of wires.

6. The system as recited in claim 1, wherein said communication is accomplished by a wireless means.

7. The system as recited in claim 1, wherein said apparatus includes a means to condense the individual's breath to form a liquid pool in contact with said sensor.

8. The system as recited in claim 7, wherein said apparatus has a means to continuously circulate and replace said sample of liquefied breath with a fresh sample of liquefied condensed breath.

9. A system for monitoring and diagnosing a respiratory condition:
    an apparatus for exposing a sensor to an individual's breath;
    said sensor exposed to an electronically activated cooling means, said cooling means functions to reduce the temperature of said sensor below the dew point of said individual's breath;
    a processing receiver;
    said sensor providing a continuous, real-time signal indicative of breath chemistry to said receiver; and
    said processing receiver processing said information for determining various diagnoses.

10. The system as recited in claim 9, wherein said apparatus is a general mask.

11. The system as recited in claim 9, wherein said respiratory condition is asthma.

12. The system as recited in claim 9, wherein said communication is accomplished by a plurality of wires.

13. The system as recited in claim 9, wherein said communication is accomplished by a wireless means.

14. The system as recited in claim 9, wherein said sensor is designed to monitor pH.

15. The system as recited in claim 9, wherein said apparatus includes a means to condense the individual's breath to form a liquid pool in contact with said sensor.

16. The system as recited in claim 15, wherein said apparatus has a means to continuously circulate and replace said sample of liquefied breath with a fresh sample of liquefied condensed breath.

17. A system for monitoring, diagnosing, and treating a respiratory condition:
    an apparatus for exposing a pH sensor to an individual's breath;
    said sensor in close proximity to an electronically activated cooling means, said cooling means functions to reduce the temperature of said sensor below the dew point of said individual's breath;

a processing receiver;

said sensor providing a continuous, real-time signal indicative of breath chemistry to said receiver;

said processing receiver processing said information for determining various diagnoses and treatments; and said processing receiver in a second communication with at least one treatment device to administer at least one therapeutic dose.

18. The system as recited in claim 17, wherein said apparatus is a general mask.

19. The system as recited in claim 17, wherein said respiratory condition is asthma.

20. The system as recited in claim 17, wherein said first communication is accomplished by a plurality of wires.

21. The system as recited in claim 17, wherein said first communication is accomplished by a wireless means.

22. The system as recited in claim 17, wherein said second communication is accomplished by a plurality of wires.

23. The system as recited in claim 17, wherein said second communication is accomplished by a wireless means.

24. The system as recited in claim 17, wherein said sensor is designed to monitor pH.

25. The system as recited in claim 17, wherein said treatment is a biocompatible agent capable of neutralizing an acidic condition.

26. The system as recited in claim 17, wherein said treatment is sodium bicarbonate.

27. The system as recited in claim 17, further comprising a communication between said processing receiver and a nebulizer/atomizer/humidifier.

28. The system as recited in claim 17, further comprising a third communication between said processing receiver and a continuous positive airway pressure device.

29. The system as recited in claim 17, wherein said apparatus includes a means to condense the individual's breath to form a liquid pool in contact with said sensor.

30. The system as recited in claim 29, wherein said apparatus has a means to continuously circulate and replace said sample of liquefied breath with a fresh sample of liquefied condensed breath.

31. An apparatus for monitoring breath chemistry comprising:

a sensor;

an electronically activated cooling means, said cooling means in physical engagement with said sensor;

said cooling means reducing the temperature of said sensor below the dew point of a patient's breath such that the patient's breath condenses into a liquid; and said sensor at least partially immersed into said liquefied breath to provide an output of a parameter of the breath.

32. An apparatus as recited in claim 31, further comprising an exit means to expel and replenish liquefied patient's breath condensate.

33. A method of monitoring a respiratory condition:

monitoring a chemical parameter of a patient's breath with a pH sensor, said sensor in close proximity with an electronically activated cooling means, said cooling means functions to reduce the temperature of said sensor below the dew point of said individual's breath; and communicating said chemical parameter in real-time under a sampling frequency from said sensor to a computing receiver.

34. A method of monitoring and diagnosing a respiratory condition:

monitoring a chemical parameter of a patient's breath with a pH sensor, said sensor in close proximity with an electronically activated cooling means, said cooling means functions to reduce the temperature of said sensor below the dew point of said individual's breath;

communicating said chemical parameter in real-time under a sampling frequency from said sensor to a computing receiver; and processing said chemical parameter information by a computing receiver to diagnose a patients' breath chemistry.

35. A method of monitoring, diagnosing and treating a respiratory condition:

monitoring a chemical parameter of a patient's breath with a pH sensor, said sensor in close proximity with an electronically activated cooling means, said cooling means functions to reduce the temperature of said sensor below the dew point of said individual's breath;

communicating said chemical parameter in real-time under a sampling frequency from said sensor to a computing receiver;

processing said chemical parameter information by a computing receiver to diagnose a patients' breath chemistry;

performing a function on the occurrence of a threshold level; and communicating with a treatment nebulizer/atomizer/humidifier such that when the chemical parameter threshold level is reached, said computing receiver instructs said treatment nebulizer/atomizer/humidifier to dispense one or more medicaments.

36. A method of monitoring a respiratory condition:

exposing a sensor to an environment that assesses a chemical parameter of the breath of a patient, said sensor in close proximity with an electronically activated cooling means, said cooling means functions to reduce the temperature of said sensor below the dew point of said individual's breath;

transferring in real-time said chemical parameter information to a processing receiver; and converting the chemical parameter information communicated to the processing receiver to a digitized format.

37. A method of monitoring and diagnosing a respiratory condition:

exposing a sensor to an environment that assesses a chemical parameter of the breath of a patient, said sensor in close proximity with an electronically activated cooling means, said cooling means functions to reduce the temperature of said sensor below the dew point of said individual's breath;

transferring in real-time said chemical parameter information to a processing receiver; and converting the chemical parameter information communicated to the processing receiver to a digitized format to diagnose said chemical parameter information.

38. A method of monitoring, diagnosing and treating a respiratory condition:

exposing a sensor to an environment that assesses a chemical parameter of the breath of a patient, said sensor in close proximity with an electronically activated cooling means, said cooling means functions to reduce the temperature of said sensor below the dew point of said individual's breath;

transferring in real-time said chemical parameter information to a processing receiver;

converting the chemical parameter information communicated to the processing receiver to a digitized format to diagnose said chemical parameter information; and processing said chemical parameter information for determining various treatments.

* * * * *